United States Patent
Gulcan et al.

(10) Patent No.: US 9,586,925 B2
(45) Date of Patent: Mar. 7, 2017

(54) 1-(DIMETHYLAMINO)ETHYL-SUBSTITUTED 6H-BENZO[C]CHROMEN-6-ONES AGAINST SENILE DEMENTIA

(71) Applicants: NOBEL ILAÇ SANAYII VE TICARET A.S., Istanbul (TR); Hayrettin Ozan Gulcan, Düzce (TR); Serdar Unlu, Düzce (TR); Ilker Esiringu, Düzce (TR); Yasemin Sahin, Düzce (TR); Tugba Ercetin, Düzce (TR); Demet Oz, Düzce (TR); Fethi Sahin, Düzce (TR)

(72) Inventors: Hayrettin Ozan Gulcan, Düzce (TR); Serdar Unlu, Düzce (TR); Ilker Esiringu, Düzce (TR); Yasemin Sahin, Düzce (TR); Tugba Ercetin, Düzce (TR); Demet Oz, Düzce (TR); Fethi Sahin, Düzce (TR)

(73) Assignee: NOBEL ILAÇ SANAYII VE TICARET A.S., Istanbul (TR)

( * ) Notice: Subject to any disclaimer, the term of this patent is extended or adjusted under 35 U.S.C. 154(b) by 0 days.

(21) Appl. No.: 14/767,431

(22) PCT Filed: Feb. 6, 2014

(86) PCT No.: PCT/TR2014/000028
§ 371 (c)(1),
(2) Date: Aug. 12, 2015

(87) PCT Pub. No.: WO2014/129990
PCT Pub. Date: Aug. 28, 2014

(65) Prior Publication Data
US 2016/0002194 A1    Jan. 7, 2016

(30) Foreign Application Priority Data
Feb. 21, 2013   (TR) .................. 2013/02067

(51) Int. Cl.
*C07D 311/80* (2006.01)

(52) U.S. Cl.
CPC .................. *C07D 311/80* (2013.01)

(58) Field of Classification Search
CPC ..................................... C07D 311/80
See application file for complete search history.

(56) References Cited

U.S. PATENT DOCUMENTS

2005/0171079 A1   8/2005 Schrimpf et al.

OTHER PUBLICATIONS

Written Opinion for International Patent Application No. PCT/TR2014/000028, mailed May 21, 2014 (6 pages).
International Preliminary Report on Patentability for International Patent Application No. PCT/TR2014/000028, mailed Jun. 2, 2015 (15 pages).
Communication under Rule 71(3) EPC for European Patent Application No. 14718201.8, mailed Feb. 23, 2016 (6 pages).
Pisani et al., "Design, synthesis, and biological evaluation of coumarin derivatives tethered to an edrophonium-like fragment as highly potent and selective dual binding site acetylcholinesterase inhibitors," ChemMedChem. 5(9):1616-30 (2010).
International Search Report for PCT/TR2014/000028, mailed May 21, 2014 (3 pages).
Piazzi, et al., "3-(4[[Benzyl(methyl)amino]methyl]phenyl)-6,7-dimethoxy-2H-2-chromenone (AP2238) inhibits both acetylcholinesterase and acetylcholinesterase-induced beta-amyloid aggregation: a dual function lead for Alzheimer's disease therapy," J Med Chem. 46(12):2279-82 (2003).

*Primary Examiner* — Noble Jarrell
*Assistant Examiner* — John S Kenyon
(74) *Attorney, Agent, or Firm* — Clark & Elbing LLP

(57) ABSTRACT

This invention relates to novel (±)1-(Dimethylamino)ethyl substituted 6H-benzo[c]chromen-6-one compounds which are useful as pharmaceutical compositions.

19 Claims, No Drawings

1-(DIMETHYLAMINO)ETHYL-SUBSTITUTED 6H-BENZO[C]CHROMEN-6-ONES AGAINST SENILE DEMENTIA

This invention relates to novel (±)1-(Dimethylamino) ethyl substituted 6H-benzo[c]chromen-6-one compounds which are useful as pharmaceutical compositions. This invention further relates to pharmaceutical compositions having benefit in the therapy for the senile dementia, such as Alzheimer senile dementia.

Senile dementia, in particular the Alzheimer senile dementia, has devastating effects on life quality of patients and their relatives. The socioeconomical burden resulting in due to the absolute need for a comprehensive medicare for sufferers of dementia completely presents the dementia accompanying diseases, in particular the Alzheimer's disease, one of the most important health issues of the new millennium awaiting new medicinal alternatives. Therefore, there is a certain need for new medications in the treatment of various forms of dementia, in particular the Alzheimer senile dementia.

Numerous targets, including the β-amyloid formation and hydrolysis cascade, several neurotransmitter formation and hydrolysis pathways, mitochondrial targets and others, have all been examined so far for the treatment of dementia, although only one of them, the cholinergic hypothesis, has been still the only validated pharmaceutical approach in the treatment of the symptoms of dementia, in particular the Alzheimer senile dementia, since, beside the NMDA receptor antagonist drug, memantine, the currently prescribed drugs (i.e., donepezil, galantamine, and rivastigmine), all belong to the acetylcholinesterase (ACHE) and butyrylcholinesterase (BCHE) inhibitor class.

Beginning from the discovery of the importance of acetylcholine function in cognitive abilities, including the social lives, natural habits, behaviors, personal characteristics, the mental processes such as interaction (i.e., understanding, speaking, observation) with the environment, attention, problem-solving, remembering, and reminding, acetylcholine-acting receptors and acetylcholine hydrolyzing enzymes have attracted the attention for the development of drugs having beneficiary effects in the relief of symptoms of dementia, particularly, the Alzheimer senile dementia. These attempts have contributed to the development of ACHE and BCHE inhibitor compounds (i.e., tacrine, donepezil, rivastigmine, and galantamine).

Unfortunately, the number of these drugs is quite a few, and there are not too many alternatives. In fact, due to the serious hepatotoxic effects of tacrine, there are only 3 drugs on the market in the ACHE inhibitor class. Therefore, there is definitely a need for more alternatives in this class of compounds.

In addition, the clinical efficiency of these drugs shows great variance among patients. Furthermore, their benefit is limited with time which means less beneficiary effect is seen with these drugs after sometime following the starting of the treatment. This also indicates the need for new drugs that might possess different characteristics in terms of the prevention of cognitive decline as well as the conservation of the cognitive status from getting worse in a longer period of treatment.

Regarding the inhibitory potential of ACHE and BCHE inhibitor drugs currently prescribed on the market (i.e., donepezil, rivastigmine, and galantamine), these drugs have quite different characteristics in terms of the inhibition of the two enzymes. First of all, galantamine and donepezil are ACHE selective inhibitors, while rivastigmine appear to possess BCHE selectivity. In addition, they have quite distinctive $IC_{50}$ values for the inhibition of ACHE and BCHE enzymes. For instance, donepezil has an $IC_{50}$ for ACHE at a very low nM level in comparison to the $IC_{50}$ of galantamine for ACHE which is close to 1 μM level. The potential of rivastigmine to inhibit both enzymes is quite different, since the $IC_{50}$ of this drug for both enzymes are above 10 μM level, although this drug has selectivity for BCHE. This definitely indicates the need of novel medicines having the potential to inhibit the both enzymes with different characteristics including less selectivity.

By the present invention an intensive and extensive investigation on 6H-benzo[c]chromen-6-one compounds have been performed and surprisingly found out that the (±)1-(Dimethylamino)ethyl substituted 6H-benzo[c]chromen-6-one compounds have benefit in the therapy for the senile dementia, such as the Alzheimer senile dementia.

Hydroxylated 6H-benzo[c]chromen-6-one compounds, also referred to as urolithins, are metabolites produced by human colonic microflora following the digestion of most of the berries, walnut, and pomegranate. These compounds are not potential inhibitors of ACHE and BCHE enzymes in comparison to the current ACHE and BCHE inhibitor drugs (i.e., donepezil, rivastigmine, and galantamine). Therefore, urolitihins have no use in the treatment of dementia, particularly the Alzheimer senile dementia, via the employment of the cholinergic hypothesis that involves the inhibition of ACHE and BCHE enzymes. Furthermore, urolithins are not drugs used in the treatment of dementia, particularly in Alzheimer senile dementia.

By this research subjected to the invention, surprisingly found that these xenobiotics can be converted to potent ACHE and BCHE inhibitors that have activity comparable to the current ACHE and BCHE inhibitor drugs (i.e., donepezil, rivastigmine, and galantamine).

Thus according to the present invention there is now provided the compounds of general formula I or a pharmaceutical acceptable salt thereof as a racemic mixture or a single enantiomer

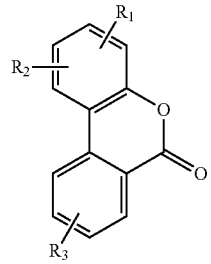

Formula I wherein;

$R_1$ is —CH(CH$_3$)N(CH$_3$)$_2$ in racemic form or a single enantiomer;

$R_2$ is selected from —H, —OH, —OCH$_3$ or —OCON(CH$_3$)(C$_2$H$_5$);

$R_3$ is selected from —H, a halogen, an alkyl, or an alkoxy group and can be in any position and positions of $R_1$ and $R_2$ are interchangeable.

In a preferred embodiment of the present invention compounds of general formula II or a pharmaceutical acceptable salt thereof as a racemic mixture or a single enantiomer are provided;

Formula II

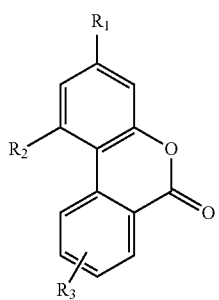

wherein;
R₁ is —CH(CH₃)N(CH₃)₂ in racemic form or a single enantiomer;
R₂ is selected from —H, —OH, —OCH₃ or —OCON(CH₃)(C₂H₅);
R₃ is H;
and positions of R₁ and R₂ are interchangeable.

Preferable compounds of the invention bearing the formula II structure include:
(R)-3-(1-(dimethylamino)ethyl)-6H-benzo[c]chromen-6-one.
(S)-3-(1-(dimethylamino)ethyl)-6H-benzo[c]chromen-6-one.
(R)-3-(1-(dimethylamino)ethyl)-1-methoxy-6H-benzo[c]chromen-6-one.
(S)-3-(1-(dimethylamino)ethyl)-1-methoxy-6H-benzo[c]chromen-6-one.
(R)-1-(1-(dimethylamino)ethyl)-3-methoxy-6H-benzo[c]chromen-6-one.
(S)-1-(1-(dimethylamino)ethyl)-3-methoxy-6H-benzo[c]chromen-6-one.
(R)-3-(1-(dimethylamino)ethyl)-1-hydroxy-6H-benzo[c]chromen-6-one.
(S)-3-(1-(dimethylamino)ethyl)-1-hydroxy-6H-benzo[c]chromen-6-one.
(R)-1-(1-(dimethylamino)ethyl)-3-hydroxy-6H-benzo[c]chromen-6-one.
(S)-1-(1-(dimethylamino)ethyl)-3-hydroxy-6H-benzo[c]chromen-6-one.
(R)-3-(1-(dimethylamino)ethyl)-6-oxo-6H-benzo[c]chromen-1-yl-ethyl(methyl)carbamate.
(S)-3-(1-(dimethylamino)ethyl)-6-oxo-6H-benzo[c]chromen-1-yl ethyl(methyl)carbamate.
(R)-1-(1-(dimethylamino)ethyl)-6-oxo-6H-benzo[c]chromen-3-yl ethyl(methyl)carbamate.
(S)-1-(1-(dimethylamino)ethyl)-6-oxo-6H-benzo[c]chromen-3-yl ethyl(methyl)carbamate.

In addition, the present invention provides a therapeutically composition which comprises a pharmacologically effective amount of the compound having the formula II or pharmacologically acceptable salt thereof and a pharmacologically acceptable carrier and then a method for preventing and treating a disease due to acetylcholinesterase or butyrylcholinesterase activity by administering to a human patient the compound having the formula I or pharmacologically acceptable salts thereof. Furthermore, the enantiomers of the compounds of the present invention described in Formula I provides a therapeutically composition alone or in racemic mixtures which comprises a pharmacologically effective amount of the compound or pharmacologically acceptable salt thereof and a pharmacologically acceptable carrier and then a method for preventing and treating a disease due to acetylcholinesterase or butyrylcholinesterase activity by administering to a human patient.

The compounds of the present invention may be prepared by various processes.

A process for the preparation of formula II or a pharmaceutical acceptable salt thereof as a racemic mixture or a single enantiomer, Formula II

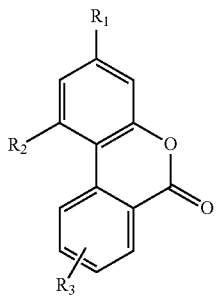

wherein;
R₁ is —CH(CH₃)N(CH₃)₂ in racemic form or a single enantiomer;
R₂ is selected from —H, —OH, —OCH₃ or —OCON(CH₃)(C₂H₅);
R₃ is H;
and positions of R₁ and R₂ are interchangeable;
comprises the steps where (1-(dimethylamino)ethyl)-substituted-phenol compound (formula III) in racemic form or a single enantiomer,
formula III, Formula III

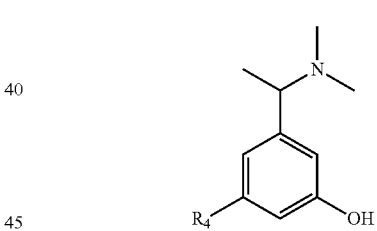

wherein R₄ is selected from —H or —OCH₃;
is reacted with a 2-halobenzoic acid compound, in the presence of polyphosphoric acid to form an ester intermediate of formula IV, Formula IV

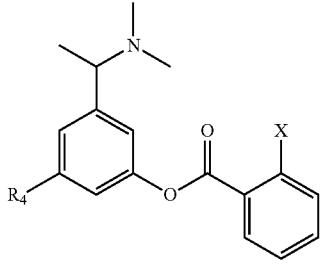

wherein R₄ is same as described above, and X is a halogen, and formula IV in racemic form or a single enantiomer, is reacted with PdCl$_2$(PPh$_3$)$_2$ in the presence of NaOAc in dimethylacetamide to obtain the compound of formula V

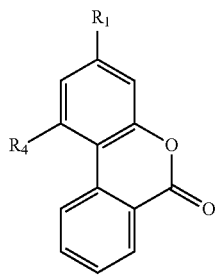

Formula V wherein R$_1$ and R$_4$ are as described above;

treatment of formula V with a hydrolyzing agent to obtain formula II wherein R$_2$ is OH;

and treatment of formula V with a carbomoyl halide compound to obtain formula II wherein R$_2$ is —OCON(CH$_3$)(C$_2$H$_5$).

Representative examples for the preparation of the compounds having the formula II are described below:

EXAMPLE I (±)-3-(1-(dimethylamino)ethyl)phenol

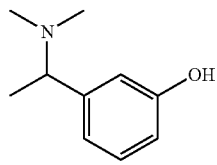

A mixture of 27.23 gram 3-hydroxyacetophenone (0.2 mol), 3.60 gram dimethylamine hydrochloride (0.4 mol), 10 gram activated molecular sieve (3 Å) and 10 gram dry MgSO$_4$ is refluxed in dry methanol for 1-2 hours. Then, 18.85 gram NaCNBH$_3$ is added to reaction mixture and the mixture is refluxed for additional 18-20 hours. After hot filtration of reaction mixture, methanol is distilled out under vacuum and the residue thus obtained is dissolved in water (250 mL). The content is acidified with conc. HCl to pH 1 and extracted with ethyl acetate (3×100 mL). The aqueous solution is basified to pH 8-9 using NaHCO$_{3(s)}$ and extracted with ethyl acetate (5×100 mL). Combined ethyl acetate extracts are washed with water dried over MgSO$_4$ and concentrated under reduced pressure to give thick oil. This oil is dissolved in isopropyl ether (120 mL) under heating and allowed to cool to 0° C. The crystalline solid obtained is filtered at the Buchner funnel under vacuum and dried in oven at 60° C. to give the product as a light yellow crystalline solid. Yield obtained: 56.0%. Purity by HPLC: 99%. Mass spectrometry: peak at m/z 166 (M+1)$^+$. $^1$H-NMR data in CD$_3$OD: δ 1.34 (d, 3H), 2.17 (s, 6H), 3.22 (q, 1H), 6.63-6.68 (m, 1H), 6.69-6.79 (m, 2H), 7.10 (t, 1H).

EXAMPLE II (±)-3-(1-(dimethylamino)ethyl)phenyl 2-bromobenzoate

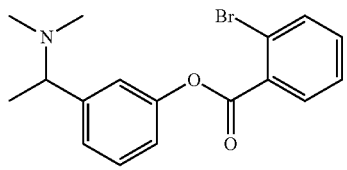 [SMILES: CC(c1cccc(OC(=O)c2ccccc2Br)c1)N(C)C]

A mixture of 1.65 gram (±)-3-(1-(dimethylamino)ethyl)phenol (10.0 mmol) and 2.2 gram 2-bromobenzoic acid (11.0 mmol) is heated in polyphosphoric acid at 80° C. for 10-15 minutes. After complete disappearance of aminophenol derivative, checked by TLC, the reaction vessel put into the ice-bath. Then, 100 mL ethylacetate and 100 mL water are added to reaction mixture respectively and pH of the content is adjusted to 8-9 using NaHCO$_{3(s)}$. Organic phase is separated from aqueous phase and then resulted water phase is extracted with ethyl acetate (3×100 mL). Combined ethyl acetate extracts are washed with water dried over MgSO$_4$ and concentrated under reduced pressure to give oily ester product. Yield obtained: 78.0%. Mass spectrometry: peak at m/z 348 (M+1)$^+$. $^1$H NMR (300 MHz, CDCl$_3$, ppm): δ 1.36 (d, 3H), 2.17 (s, 6H), 3.26 (q, 1H), 7.04-7.21 (m, 3H), 7.26-7.41 (m, 3H), 7.63-7.70 (m, 1H), 7.91-7.99 (m, 1H).

EXAMPLE III

FAR-02-2RS (±)-3-(1-(dimethylamino)ethyl)-6H-benzo[c]chromen-6-one

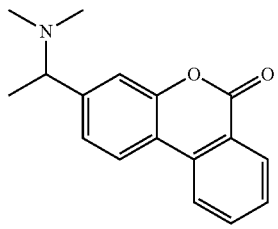 [SMILES: CC(c1ccc2c(c1)oc(=O)c1ccccc12)N(C)C]

To a solution of (±)-3-(1-(dimethylamino)ethyl)phenyl 2-bromobenzoate (1.006 gram, 4.05 mmol) in 35 mL of dry DMA, NaOAc (664 mg, 8.1 mmol) and PdCl$_2$(PPh$_3$)$_2$ (284 mg, 0.405 mmol) were added at 80° C. After stirring the reaction mixture at 130° C. for 15-16 h, the solvent was evaporated under reduced pressure. The content is acidified with 1 N HCl (200 mL) and extracted with ethyl acetate (3×75 mL). The aqueous solution is basified to pH 8-9 using NaHCO$_{3(s)}$ and extracted with ethyl acetate (5×100 mL). Combined ethyl acetate extracts are dried over MgSO$_4$ and concentrated under reduced pressure to give yellow thick oil. Column chromatography on silica gel employing acetone gives desired benzo[c]chromen-6-one derivative (526 mg, 68.0%).

EXAMPLE IV (±)-3-(1-(dimethylamino)ethyl)-6H-benzo[c]chromen-6-one hydrochloride 2.0 Gram (7.49 mmol) 3-(1-(dimethylamino)ethyl)-6H-benzo[c]chromen-6-one (free base) dissolved in dry acetone (10 mL) is filtrated from 0.45 μm filter. HCl gas is passed through the obtained acetone solution until salt precipitation takes place. The content is mixed for additional 1 hour and then filtrated. The retentate is dried at 40° C. under vacuum. Yield obtained: 81.0%, HPLC purity: 99.90%, HRMS(ESI) $C_{17}H_{18}NO_2$ calcd 268.1338 (M+1)$^+$. found 268.1330, DSC: 235.40° C., $^1$H NMR (300 MHz, DMSO, ppm): δ 1.67 (d, 3H), 2.52 (s, 3H), 2.72 (s, 3H), 4.56 (q, 1H), 7.60-7.73 (m, 3H), 7.94 (dt, 1H), 8.22 (dd, 1H), 8.39-8.49 (m, 2H), 11.40 (brs, 1H).

EXAMPLE V (S)-3-(1-(dimethylamino)ethyl)phenyl 2-bromobenzoate

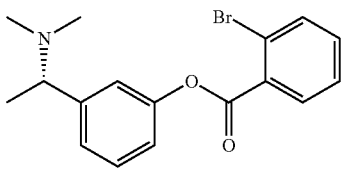

The desired ester derivative is synthesized according to procedure given in Example II. Yield obtained: 78.0%. Mass spectrometry: peak at m/z 348 (m+1). $^1$H NMR (300 MHz, CDCl$_3$, ppm): δ 1.36 (d, 3H), 2.17 (s, 6H), 3.26 (q, 1H), 7.04-7.21 (m, 3H), 7.26-7.41 (m, 3H), 7.63-7.70 (m, 1H), 7.91-7.99 (m, 1H).

EXAMPLE VI

FAR-02-2S (S)-3-(1-(dimethylamino)ethyl)-6H-benzo[c]chromen-6-one

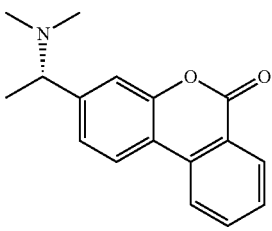 [SMILES: C[C@@H](c1ccc2c(c1)oc(=O)c1ccccc12)N(C)C]

The target molecule is synthesized according to procedure given in Example III. Yield obtained: 66.0%

EXAMPLE VII (S)-3-(1-(dimethylamino)ethyl)-6H-benzo[c]chromen-6-one.HCl

The desired salt form is synthesized according to procedure given in Example IV. Yield obtained: 83.0%. HPLC purity: 99.95%, HRMS(ESI) $C_{17}H_{18}NO_2$ calcd 268.1338 (M+1)$^+$. found 268.1341, DSC: 254.13° C., $^1$H NMR (300 MHz, DMSO, ppm): δ 1.66 (d, 3H), 2.51 (d, 3H), 2.72 (d, 3H), 4.50-4.62 (m, 1H), 7.59-7.74 (m, 3H), 7.92 (dt, 1H), 8.22 (dd, 1H), 8.37-8.49 (m, 2H), 11.36 (brs, 1H).

EXAMPLE VIII 1-(3-hydroxy-5-methoxyphenyl)ethanone

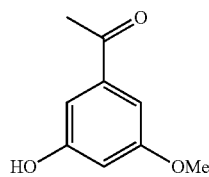

Procedure A: 6.2 gram NaOH (0.150 mol) is dissolved in 125 mL water. 25 gram 3,5-dihydroxyacetophenone (0.160 mol) is weighted in 250 mL round bottom flask and previously prepared NaOH solution is added to the flask. After complete disolvation of acetophenone derivative in basic aqueous media, the reaction mixture is cooled to 0-10° C. Then, 19.5 gram DMS (0.156 mol) is added to reaction flask dropwise. The content is mixed at ambient temperature for one hour, and then it is heated at 50° C. for two hours. To separate 3,5-dimethoxyacetophenone impurity, pH of medium is adjusted to 14 with NaOH pellet and this solution is extracted with EtOAc (3×50 mL). The alkali solution is acidified with conc HCl to pH 1 and extracted with ethyl acetate (3×75 mL). Combined ethyl acetate extracts are dried over MgSO$_4$ and concentrated under reduced pressure to give mixture of 3,5-dihydroxyacetophenone and 1-(3-hydroxy-5-methoxyphenyl)ethanone. To the mixture, 50 mL asetone and 25 gram NaOH$_{(s)}$ is added. When, 8-10 mL cold water is put into the reaction flask slowly, sodium salt of 3,5-dihydroxyacetophenone is precipitated. The liquid part of the content is decanteted to another round bottom flask. The solid part is washed with asetone (3×15 mL). Combined asetone parts concentrated under reduced pressure to give 1-(3-hydroxy-5-methoxyphenyl)ethanone as off white solid. Yield obtained: 56.2%. Mass spectrometry: peak at m/z 166 (m+1). $^1$H NMR (300 MHz, CDCl$_3$, ppm): δ 2.56 (s, 3H), 3.79 (s, 3H), 6.62-6.67 (m, 2H), 7.01-7.05 (m, 1H), 7.07-7.11 (m, 1H).

Procedure B: 11.36 mL NEt$_3$ (82.14 mmol) is added to 137 mL water. 25 gram 3,5-dihydroxyacetophenone (0.160 mol) is weighted in 250 mL round bottom flask and previously prepared NEt$_3$ solution is added to the flask. The reaction mixture is cooled to 0-10° C. Then, 7.78 mL DMS (82.14 mol) is added to reaction flask dropwise. The content is mixed at ambient temperature for 4 hours. After the reaction mixture is cooled 0-5° C., the content is filtrated to remove undissolved 3,5-dihydroxyacetophenone. pH of filtrate is adjusted to 1 with conc. HCl and exctacted with EtOAc (3×50 mL). Combined ethyl acetate extracts are dried over MgSO$_4$ and concentrated under reduced pressure to give mixture of 3,5-dihydroxyacetophenone and 1-(3-hydroxy-5-methoxyphenyl)ethanone. To the mixture, 50 mL asetone and 25 gram NaOH$_{(s)}$ is added. When, 8-10 mL cold water is put into the reaction flask slowly, sodium salt of 3,5-dihydroxyacetophenone is precipitated. The liquid part of the content is decanteted to another round bottom flask. The solid part is washed with asetone (3×15 mL). Combined asetone parts concentrated under reduced pressure to give 1-(3-hydroxy-5-methoxyphenyl)ethanone as off white solid. Yield obtained: 44.7%, Mass spectrometry: peak at m/z 166

(M+1)⁺. ¹H NMR (300 MHz, CDCl₃, ppm): δ 2.56 (s, 3H), 3.79 (s, 3H), 6.62-6.67 (m, 2H), 7.01-7.05 (m, 1H), 7.07-7.11 (m, 1H).

EXAMPLE IX (±)-3-(1-(dimethylamino)ethyl)-5-methoxyphenol

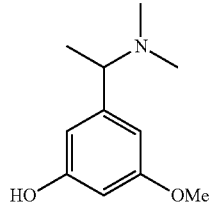

The desired aminophenol derivative is synthesized according to procedure given in Example I. Yield obtained: 60.6%. Mass spectrometry: peak at m/z 196 (M+1)⁺. ¹H NMR (300 MHz, CDCl₃, ppm): δ 1.29 (d, 3H), 2.13 (s, 6H), 3.15 (q, 1H), 3.61 (s, 3H), 6.21 (t, 1H), 6.24-6.27 (m, 1H), 6.29-6.31 (m, 1H), 8.32 (brs, 1H).

EXAMPLE X (±)-3-(1-(dimethylamino)ethyl)-5-methoxyphenyl 2-bromobenzoate

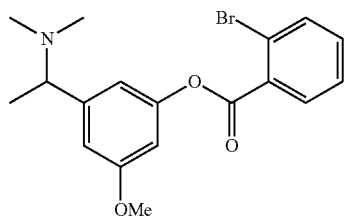 [SMILES: COc1cc(OC(=O)c2ccccc2Br)cc(C(C)N(C)C)c1]

The desired ester derivative is synthesized according to procedure given in Example II. Yield obtained: 70.2%. Mass spectrometry: peak at m/z 378 (M+1)⁺. ¹H NMR (300 MHz, CDCl₃, ppm): δ 1.33 (d, 3H), 2.19 (s, 6H), 3.23 (q, 1H), 3.75 (s, 3H), 6.64 (t, 1H), 6.75 (d, 2H), 7.32-7.39 (m, 2H), 7.64-7.69 (m, 1H), 7.92-7.97 (m, 1H).

EXAMPLE XI

FAR-01-2

(±)-3-(1-(dimethylamino)ethyl)-1-methoxy-6H-benzo[c]chromen-6-one

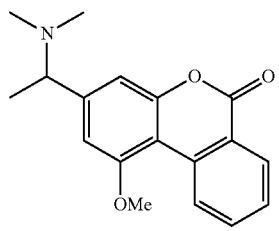 [SMILES: COc1cc(C(C)N(C)C)cc2oc(=O)c3ccccc3c12]

The target molecule is synthesized according to procedure given in Example III. Yield obtained: 46.2%

EXAMPLE XII (±)-3-(1-(dimethylamino)ethyl)-1-methoxy-6H-benzo[c]chromen-6-one hydrochloride The desired salt form is synthesized according to procedure given in Example IV. Yield obtained: 81.3%. HPLC purity: 99.40%, HRMS(ESI) C₁₈H₂₀NO₃ calcd 298.1443 (M+1)⁺. found 298.1433, DSC: 247.8° C., ¹H NMR (300 MHz, DMSO, ppm): δ 1.68 (d, 3H), 2.56 (d, 3H), 2.76 (d, 3H), 4.07 (s, 3H), 4.51 (q, 1H), 7.27 (d, 1H), 7.47 (s, 1H), 7.65 (dt, 1H), 7.90 (dt, 1H), 8.25 (dd, 1H), 8.93 (d, 1H), 11.41 (brs, 1H).

EXAMPLE XIII

FAR-01-1

(±)-1-(1-(dimethylamino)ethyl)-3-methoxy-6H-benzo[c]chromen-6-one

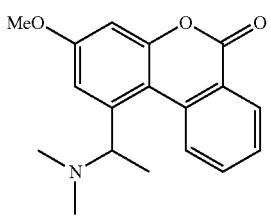 [SMILES: COc1cc(C(C)N(C)C)c2c(c1)oc(=O)c1ccccc12]

The target molecule is synthesized according to procedure given in Example III. Yield obtained: 14.2%

EXAMPLE XIV (±)-1-(1-(dimethylamino)ethyl)-3-methoxy-6H-benzo[c]chromen-6-one hydrochloride The desired salt form is synthesized according to procedure given in Example IV. Yield obtained: 83.7%, HPLC purity: 99.90%, HRMS(ESI) C₁₈H₂₀NO₃ calcd 298.1443 (M+1)⁺. found 298.1431, DSC: 110.42° C., ¹H NMR (300 MHz, CD₃OD, ppm): δ 1.54 (d, 3H), 2.18 (s, 6H), 3.86 (s, 3H), 4.15 (q, 1H), 6.81 (d, 1H), 7.24 (d, 1H), 7.53 (dt, 1H), 7.82 (dt, 1H), 8.20 (brs, 1H), 8.28 (dd, 1H).

EXAMPLE XV

FAR-01-2OH (±)-3-(1-(dimethylamino)ethyl)-1-hydroxy-6H-benzo[c]chromen-6-one

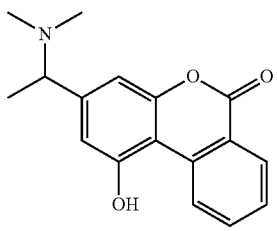 [SMILES: CC(c1cc(O)c2c(c1)oc(=O)c1ccccc12)N(C)C]

To (±)-3-(1-(dimethylamino)ethyl)-1-methoxy-6H-benzo[c]chromen-6-one (4.60 gram, 15.47 mmol) is added 48% aqueous HBr (190 mL) at room temperature. The mixture was heated at 130° C. for 20-24 hours. After cooling, the aqueous solution is basified to pH 8-9 using $NaHCO_{3(s)}$ and extracted with $CH_2Cl_2$ (4×50 mL). Combined $CH_2Cl_2$ extracts are dried over $MgSO_4$ and concentrated under reduced pressure to give yellow-brown oil. Column chromatography on silica gel employing acetone gave desired benzo[c]chromen-6-one derivative (1.37 gram, 31.0%).

EXAMPLE XVI (±)-3-(1-(dimethylamino)ethyl)-1-hydroxy-6H-benzo[c]chromen-6-one hydrochloride 1.37 gram (4.8 mmol) (±)-3-(1-(dimethylamino)ethyl)-1-hydroxy-6H-benzo[c]chromen-6-one (free base) dissolved in 30 mL dry metanol:asetone (1:3) is filtrated from 0.45 µm filtre. HCl gas is passed through the obtained metanol-asetone solution. Liquid part is concentrated under reduced pressure to give yellow oil. When 10 ml dry asetone is added to resulted oil, HCl salt form of 3-(1-(dimethylamino)ethyl)-1-hydroxy-6H-benzo[c]chromen-6-one is precipitated. The content is mixed for 1 hour and then filtrated. The residue is dried at 40° C. under vacuum. Yield obtained: 79.3%. HPLC purity: 99.82%, HRMS(ESI) $C_{17}H_{18}NO_3$ calcd 284.1287 $(M+1)^+$. found 284.1293, DSC: 253.54° C. $^1$H NMR (300 MHz, DMSO, ppm): δ 1.62 (d, 3H), 2.54 (s, 3H), 2.75 (s, 3H), 4.43 (q, 1H), 7.06 (s, 1H), 7.23 (s, 1H), 7.62 (t, 1H), 7.90 (dt, 1H), 8.24 (d, 1H), 9.09 (d, 1H), 11.07 (brs, 1H), 11.55 (s, 1H).

EXAMPLE XVII

FAR-01-1OH (±)-1-(1-(dimethylamino)ethyl)-3-hydroxy-6H-benzo[c]chromen-6-one

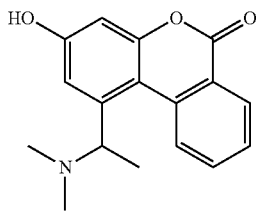

To (±)-1-(1-(dimethylamino)ethyl)-3-methoxy-6H-benzo[c]chromen-6-one (1.49 gram, 5.0 mmol) is added 48% aqueous HBr (62 mL) at room temperature. The mixture was heated at 120° C. for 4 hours. After cooling, the aqueous solution is basified to pH 8-9 using $NaHCO_{3(s)}$ and extracted with $CH_2Cl_2$ (4×40 mL). Combined $CH_2Cl_2$ extracts are dried over $MgSO_4$ and concentrated under reduced pressure to give yellow solid (1.20 gram, 84.5%).

EXAMPLE XVIII (±)-1-(1-(dimethylamino)ethyl)-3-hydroxy-6H-benzo[c]chromen-6-one.HCl The desired salt form is synthesized according to procedure given in Example IV. Yield obtained: 86.0%. HPLC purity: 99.07%, HRMS(ESI) $C_{17}H_{18}NO_3$ calcd 284.1287 $(M+1)^+$. found 284.1289, DSC: 217.01° C., $^1$H NMR (300 MHz, $CD_3OD$, ppm): δ 1.50 (d, 3H), 2.17 (s, 6H), 4.13 (q, 1H), 6.62 (d, 1H), 7.09 (s, 1H), 7.48 (t, 1H), 7.78 (dt, 1H), 8.15 (brs, 1H), 8.25 (dd, 1H).

EXAMPLE XIX

FAR-01-2CA (±)-3-(1-(dimethylamino)ethyl)-6-oxo-6H-benzo[c]chromen-1-yl ethyl(methyl)carbamate

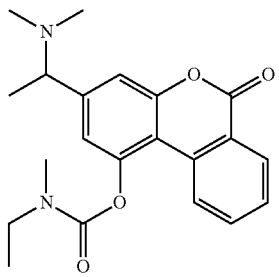 [SMILES: CCN(C)C(=O)Oc1cc(C(C)N(C)C)cc2oc(=O)c3ccccc3c12]

960 mg (±)-3-(1-(dimethylamino)ethyl)-1-hydroxy-6H-benzo[c]chromen-6-one (3.00 mmol) and 547.40 mg carbamoyl chloride (4.30 mmol) is mixed in pyridine (18 mL) at ambient temperature for 18-20 hours. Pyridine is concentrated under reduced pressure to give yellow-brown oil. Then pH is adjusted to 8-9 using saturated $NaHCO_3$ and extracted with $CH_2Cl_2$ (4×50 mL). Combined $CH_2Cl_2$ extracts are dried over $MgSO_4$ and concentrated under reduced pressure to give yellow thick oil. Column chromatography on silica gel employing acetone gives desired benzo[c]chromen-6-one derivative (1.04 gram, 95.0%).

EXAMPLE XX (±)-3-(1-(dimethylamino)ethyl)-6-oxo-6H-benzo[c]chromen-1-yl ethyl(methyl)carbamate hydrochloride 1.00 gram (2.7 mmol) (±)-3-(1-(dimethylamino)ethyl)-6-oxo-6H-benzo[c]chromen-1-yl ethyl(methyl)carbamate (free base) dissolved in 30 mL dry asetone:heptane (1:3) is filtrated from 0.45 µm filtre. HCl gas is passed through the obtained asetone-heptane solution, until salt precipitation takes place. The content is mixed for 2 hours and then filtrated. The filtrand is dried at 40° C. under vacuum. Yield obtained: 96.3%. HPLC purity: 99.16%, HRMS(ESI) $C_{21}N_{25}N_2O_4$ calcd 369.1814 $(M+1)^+$. found 369.1825, DSC: 256.35° C., $^1$H NMR (300 MHz, DMSO, ppm): δ 1.07-1.35 (m, 3H), 1.67 (d, 3H), 2.54 (d, 3H), 2.71 (d, 3H), 3.08 (d, 3H), 3.28-3.68 (m, 2H), 4.57 (q, 1H), 7.42 (s, 1H), 7.65-7.77 (m, 2H), 7.91-8.02 (m, 1H), 8.27-8.42 (m, 2H), 11.37 (brs, 1H).

EXAMPLE XXI

FAR-01-1CA (±)-1-(1-(dimethylamino)ethyl)-6-oxo-6H-benzo[c]chromen-3-yl ethyl(methyl)carbamate

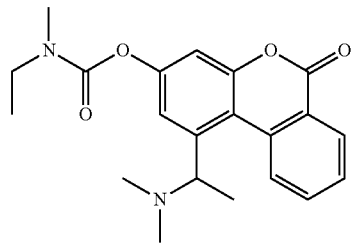 [SMILES: CCN(C)C(=O)Oc1cc(C(C)N(C)C)c2c(c1)oc(=O)c1ccccc12]

660 mg (±)-1-(1-(dimethylamino)ethyl)-3-hydroxy-6H-benzo[c]chromen-6-one (2.33 mmol) and 424.76 mg carbamoyl chloride (3.49 mmol) is mixed in pyridine (16 mL) at ambient temperature for 17-19 hours. Pyridine is concentrated under reduced pressure to give yellow-brown oil. Then pH is adjusted to 8-9 using saturated $NaHCO_3$ and extracted with $CH_2Cl_2$ (4×50 mL). Combined $CH_2Cl_2$ extracts are dried over $MgSO_4$ and concentrated under reduced pressure to give yellow thick oil. Column chromatography on silica gel (Asetone:Dichlorometan; 2:1) gave desired benzo[c]chromen-6-one derivative (511 mg, 60.0%).

EXAMPLE XXII (±)-1-(1-(dimethylamino)ethyl)-6-oxo-6H-benzo[c]chromen-3-yl ethyl(methyl)carbamate hydrochloride 511 mg (1.4 mmol) (±)-1-(1-(dimethylamino)ethyl)-6-oxo-6H-benzo[c]chromen-3-yl ethyl(methyl)carbamate (free base) dissolved in 30 mL dry eter:asetone (1:3) is filtrated from 0.45 µm filtre. HCl gas is passed through the obtained eter-asetone solution, until salt precipitation takes place. The content is mixed for 2 hours and then filtrated. The filtrand is dried at 40° C. under vacuum. Yield obtained: 71.7%. HPLC purity: 99.62%, HRMS(ESI) $C_{21}H_{25}N_2O_4$ calcd 369.1814 $(M+1)^+$. found 369.1808, DSC: 127.9° C., $^1H$ NMR (300 MHz, $CD_3OD$, ppm): δ 1.13-1.31 (m, 3H), 1.67 (d, 3H), 2.33 (s, 6H), 3.04 (d, 3H), 3.34-3.57 (m, 2H), 4.48 (brs, 1H), 7.13 (s, 1H), 7.43 (d, 1H), 7.63 (dt, 1H), 7.89 (dt, 1H), 8.16 (brs, 1H), 8.33 (dd, 1H).

The compounds of the present invention concomitant with the pharmaceutical salts thereof represented by the general formula II, including the each enantiomer, are useful in the treatment of various kinds of senile dementia, in particular Alzheimer's Disease accompanying senile dementia. Related pharmacological experimental data are described.

Experimental (Pharmacology)

The potential of the compounds of the present invention to inhibit acetylcholinesterase and butyrylcholinesterase enzymes were tested according to the method of Ellman et.al. (i.e., Ellman, G. L., Courtney, K. D., Andres, V., and Featherstone, R. M., Biochem. Pharmacol., 1961, 7, 88-95).

Human recombinant acetylcholinesterase and human recombinant butyrylcholinesterase were employed. Each reaction mixture contained the enzyme (either ACHE or BCHE) solution, DTNB and sample in Tris HCl buffer solution. The reactions were initiated by the addition of the substrate (either acetylthiocholine iodide or butyrylthiocholine iodide, respectively for ACHE and BCHE enzymes). The enzyme catalyzed formation of the yellow color was measured at 412 nm in terms of the calculation of enzyme activity concomitant to the presence of an inhibitor activity. The acetylcholinesterase and butyrylcholinesterase inhibitory activity of each sample was expressed in terms of inhibitory concentration 50% ($IC_{50}$).

Representative examples are shown in Table I:

| Compound | ACHE Inhibitory Activity $IC_{50}$ (µM) | BCHE Inhibitory Activity $IC_{50}$ (µM) | Example No. |
|---|---|---|---|
| FAR-02-2RS | 10.9 | 17.9 | III |
| FAR-02-2S | 7.9 | 16.2 | VI |
| FAR-01-2 | 2.8 | 21.1 | XI |
| FAR-01-1 | 15.1 | 24.7 | XIII |
| FAR-01-2OH | 18.9 | 4.2 | XV |
| FAR-01-1OH | 33.1 | >40 | XVII |
| FAR-01-2CA | 40.0 | 12.7 | XIX |
| FAR-01-1CA | >40 | 8.5 | XXI |
| Rivastigmine | 35.2 | 11.0 | — |
| Galantamine | 0.7 | 21.9 | — |
| Donepezil | 0.008 | 7.1 | — |

In general, the compounds of the present invention displayed strong potential for the inhibition of both ACHE and BCHE enzymes.

There are several compounds which possess strong inhibition towards BCHE. In comparison to the current drugs (i.e., galantamine, rivastigmine, and donepezil), the compounds such as FAR-01-2OH, FAR-01-2CA, and FAR-01-1CA have exhibited at least comparable and/or better inhibitory potential towards BCHE inhibition.

Although, the selectivity of the compounds of the present invention seems to be bias for the ACHE enzyme some of the compounds (i.e., FAR-01-2OH, and FAR-01-1CA) possess selectivity to inhibit the BCHE.

The diversity obtained through the different $IC_{50}$ values of the compounds of the present invention makes them alternative promising compounds in the treatment of dementia, particularly the Alzheimer senile dementia.

Experimental (Passive Avoidance Learning Test)

The passive avoidance test evaluates the ability of a rat to learn and memorize. Male Wistar rats, at an age of approximately 2 months, and around 250 g body weight were used. For learning, the rats were placed into the illuminated compartment while the door closed and allowed a habituation phase (30 seconds). Then the door automatically opened and stayed open for 5 minutes experimental time. Two seconds after the rat entering the dark compartment of the apparatus the door closed and after 2 seconds latency an electric stimulus took place lasting for 3 or 6 seconds. The rat stayed in the dark compartment for another 30 seconds delay before it was placed into the home cage.

For testing, the rats were treated with 1 mg/kg (i.p.) of scopolamine, half an hour before the administration of the each test compound. Half an hour after the oral administration of the each compound, the rats were placed into the illuminated compartment with the door closed again for a habituation time of 30 seconds. Following the opening of the door automatically, the time for the rats visiting the dark box (latency) was measured for 5 minutes. The time difference between the no scopolamine administered group and the only scopolamine administered group was taken as 100% and the effect of each compound of the present invention was calculated accordingly in terms of the percentage antagonism. Each test compound was assessed employing ten animals per dose.

The results are shown Table II:

| Compound | Dose (mg/kg) | Reverse (%) | Example No. |
| --- | --- | --- | --- |
| FAR-02-2RS | 1 | 70 | III |
| FAR-02-2S | 1 | 71 | VI |
| FAR-01-2 | 1 | 71 | XI |
| FAR-01-2OH | 1 | 49 | XV |
| FAR-01-2CA | 1 | 53 | XIX |
| Donepezil | 1 | 52 | |
| Rivastigmine | 1 | 85 | |

As seen in the Table II, the compounds of the present invention have considerable effect in the test of passive avoidance learning impairment induced by scopolamine. The results obtained through both the in-vitro acetylcholinesterase and butyrylcholinesterase inhibition tests and the in-vitro passive avoidance test present the compounds of this invention as powerful, promising, and novel compounds effective for various kinds of dementia, particularly the Alzheimer senile dementia.

The invention claimed is:

1. A compound having the following formula I or a pharmaceutically acceptable salt thereof as a racemic mixture or a single enantiomer

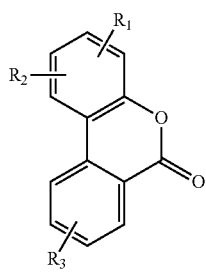

Formula I wherein:
$R_1$ is —$CH(CH_3)N(CH_3)_2$ in racemic form or a single enantiomer;
$R_2$ is selected from —H, —OH, —$OCH_3$ or —$OCON(CH_3)(C_2H_5)$;
$R_3$ is selected from —H, a halogen, an alkyl, or an alkoxy group and can be in any position
and positions of $R_1$ and $R_2$ are interchangeable.

2. The compound according to claim 1 having the following formula II or a pharmaceutically acceptable salt thereof as a racemic mixture or a single enantiomer

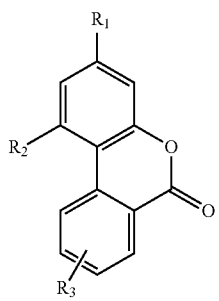

Formula II wherein:
$R_1$ is —$CH(CH_3)N(CH_3)_2$ in racemic form or a single enantiomer;
$R_2$ is selected from —H, —OH, —$OCH_3$ or —$OCON(CH_3)(C_2H_5)$;
$R_3$ is H;
and positions of $R_1$ and $R_2$ are interchangeable.

3. The compound according to claim 1, which is (R)-3-(1-(dimethylamino)ethyl)-6H-benzo[c]chromen-6-one.

4. The compound according to claim 1, which is (S)-3-(1-(dimethylamino)ethyl)-6H-benzo[c]chromen-6-one.

5. The compound according to claim 1, which is (R)-3-(1-(dimethylamino)ethyl)-1-methoxy-6H-benzo[c]chromen-6-one.

6. The compound according to claim 1, which is (S)-3-(1-(dimethylamino)ethyl)-1-methoxy-6H-benzo[c]chromen-6-one.

7. The compound according to claim 1, which is (R)-1-(1-(dimethylamino)ethyl)-3-methoxy-6H-benzo[c]chromen-6-one.

8. The compound according to claim 1, which is (S)-1-(1-(dimethylamino)ethyl)-3-methoxy-6H-benzo[c]chromen-6-one.

9. The compound according to claim 1, which is (R)-3-(1-(dimethylamino)ethyl)-1-hydroxy-6H-benzo[c]chromen-6-one.

10. The compound according to claim 1, which is (S)-3-(1-(dimethylamino)ethyl)-1-hydroxy-6H-benzo[c]chromen-6-one.

11. The compound according to claim 1, which is (R)-1-(1-(dimethylamino)ethyl)-3-hydroxy-6H-benzo[c]chromen-6-one.

12. The compound according to claim 1, which is (S)-1-(1-(dimethylamino)ethyl)-3-hydroxy-6H-benzo[c]chromen-6-one.

13. The compound according to claim 1, which is (R)-3-(1-(dimethylamino)ethyl)-6-oxo-6H-benzo[c]chromen-1-yl ethyl(methyl)carbamate.

14. The compound according to claim 1, which is (S)-3-(1-(dimethylamino)ethyl)-6-oxo-6H-benzo[c]chromen-1-yl ethyl(methyl)carbamate.

15. The compound according to claim 1, which is (R)-1-(1-(dimethylamino)ethyl)-6-oxo-6H-benzo[c]chromen-3-yl ethyl(methyl)carbamate.

16. The compound according to claim 1, which is (S)-1-(1-(dimethylamino)ethyl)-6-oxo-6H-benzo[c]chromen-3-yl ethyl(methyl)carbamate.

17. A method of treating a disease due to acetylcholinesterase and/or butyrylcholinesterase activity, said method comprising administering a compound having the formula I according to claim 1, or a pharmaceutically acceptable salt thereof, wherein the disease is senile dementia.

18. A process for the preparation of formula II or a pharmaceutically acceptable salt thereof as a racemic mixture or a single enantiomer,

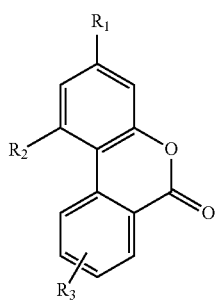

Formula II wherein;

$R_1$ is —CH(CH$_3$)N(CH$_3$)$_2$ in racemic form or a single enantiomer;

$R_2$ is selected from —H, —OH, —OCH$_3$ or —OCON(CH$_3$)(C$_2$H$_5$);

$R_3$ is H;

and positions of $R_1$ and $R_2$ are interchangeable;

said method comprising reacting a (1-(dimethylamino)ethyl)-substituted-phenol compound of formula III in racemic form or a single enantiomer,

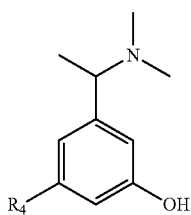

Formula III wherein $R_4$ is selected from —H or —OCH$_3$, with a 2-halobenzoic acid compound in the presence of polyphosphoric acid to form an ester intermediate of formula IV,

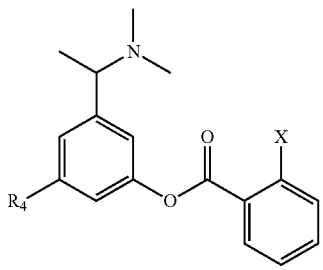

Formula IV wherein $R_4$ is as described above and X is a halogen, and reacting the ester intermediate of formula IV in racemic form or a single enantiomer with PdCl$_2$(PPh$_3$)$_2$ in the presence of NaOAc in dimethylacetamide to obtain the compound of formula V,

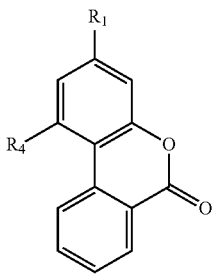

Formula V wherein $R_1$ and $R_4$ are as described above; and treating the compound of formula V with a hydrolyzing agent to obtain the compound of formula II wherein $R_2$ is OH; and treating the compound of formula V with a carbamoyl halide compound to obtain the compound of formula II wherein $R_2$ is —OCON(CH$_3$)(C$_2$H$_5$).

19. The method of claim 17, wherein said compound is (±)-3-(1-(dimethylamino)ethyl)-6-oxo-6H-benzo[c]chromen-1-ylethyl(methyl)carbamate.

* * * * *